US012112852B2

(12) United States Patent
Arteta Montilva et al.

(10) Patent No.: US 12,112,852 B2
(45) Date of Patent: Oct. 8, 2024

(54) CAD DEVICE AND METHOD FOR ANALYSING MEDICAL IMAGES

(71) Applicant: Optellum Limited, Oxford (GB)

(72) Inventors: Carlos Federico Arteta Montilva, Oxford (GB); Nicholas Dowson, Oxford (GB); Timor Kadir, Oxford (GB); Jerome Declerck, Oxford (GB)

(73) Assignee: Optellum Limited, Oxford (GB)

( * ) Notice: Subject to any disclaimer, the term of this patent is extended or adjusted under 35 U.S.C. 154(b) by 521 days.

(21) Appl. No.: 17/094,934

(22) Filed: Nov. 11, 2020

(65) Prior Publication Data

US 2022/0148727 A1    May 12, 2022

(51) Int. Cl.
*G16H 50/20* (2018.01)
*G06N 3/04* (2023.01)
(Continued)

(52) U.S. Cl.
CPC .............. *G16H 50/20* (2018.01); *G06N 3/04* (2013.01); *G06T 7/0012* (2013.01); *G16H 10/60* (2018.01); *G16H 30/40* (2018.01); *G16H 50/30* (2018.01); *G06T 2207/20081* (2013.01); *G06T 2207/20084* (2013.01); *G06T 2207/30061* (2013.01)

(58) Field of Classification Search
CPC ......... G06T 7/0012; G06T 2207/30061; G06T 2207/20081; G06T 2207/20084; G16H 50/20; G16H 10/60; G16H 50/30; G16H 30/40; G06N 3/04
See application file for complete search history.

(56) References Cited

U.S. PATENT DOCUMENTS

| 7,395,216 B2 * | 7/2008 | Rosenfeld | G16H 40/67 600/300 |
| 2009/0082637 A1 * | 3/2009 | Galperin | G16H 30/20 600/300 |

(Continued)

FOREIGN PATENT DOCUMENTS

| WO | WO-2016094330 A2 * | 6/2016 | ....... G01N 33/57423 |
| WO | WO-2017092615 A1 * | 6/2017 | .......... G06K 9/6221 |
| WO | WO-2018222755 A1 * | 12/2018 | ............. A61B 5/055 |

OTHER PUBLICATIONS

Machine translation of WO-2017092615-A1 (Year: 2017).*
(Continued)

*Primary Examiner* — Aaron W Carter
*Assistant Examiner* — Courtney Joan Nelson
(74) *Attorney, Agent, or Firm* — Optimus Patents US, LLC

(57) ABSTRACT

A method for providing a lung disease risk measure in a Computer Aided Diagnosis system is described. The method comprises the steps of: receiving an input comprising at least one input image showing all or part of the lungs of a patient; analysing the input to identify a feature descriptor comprised of at least one feature group, where each feature group comprises at least one feature computed from the input image; calculating a score explanation factor for each feature group, and an overall disease risk score for the patient's risk of lung disease from the feature descriptor; outputting the overall disease score risk score and a corresponding score explanation factor for each feature group. A computer aided diagnosis system is also described, along with a method for training a computer aided diagnosis system.

11 Claims, 6 Drawing Sheets

(51) Int. Cl.
    *G06T 7/00*         (2017.01)
    *G16H 10/60*      (2018.01)
    *G16H 30/40*      (2018.01)
    *G16H 50/30*      (2018.01)

(56) References Cited

U.S. PATENT DOCUMENTS

| | | | | |
|---|---|---|---|---|
| 2015/0088430 | A1* | 3/2015 | Whitney | G16B 25/10 |
| | | | | 435/6.12 |
| 2015/0234999 | A1* | 8/2015 | Hu | G16Z 99/00 |
| | | | | 705/2 |
| 2017/0357771 | A1* | 12/2017 | Connolly | G16H 50/30 |
| 2022/0059234 | A1* | 2/2022 | Zhao | G16H 15/00 |

OTHER PUBLICATIONS

Sriporn, K.; Tsai, C.-F.; Tsai, C.-E.; Wang, P. Analyzing Lung Disease Using Highly Effective Deep Learning Techniques. Healthcare 2020, 8, 107. https://doi.org/10.3390/healthcare8020107 (Year: 2020).*

EP Application No. 21206440.6 to Optellum Limited, EPO Article 94(3) Communication, Jan. 18, 2024.

* cited by examiner

CAD DEVICE AND METHOD FOR ANALYSING MEDICAL IMAGES

FIELD OF INVENTION

This invention relates to the field of Computer Aided Diagnosis (CADx) systems and methods for assisting the interpretation of medical images to support clinicians in healthcare. In particular, the field relates to Computer Aided Diagnosis systems used to assist the reading and reporting of medical images by radiologists and the interpretation of the radiologist's report by the physician responsible for patient care.

BACKGROUND OF INVENTION

Lung cancer remains the most common cause of cancer-related death in the UK and USA, even though lung cancer is usually curable if caught at an early stage. As a result of recent lung cancer studies, including the National Lung cancer Screening Trial (NLST) and the Dutch-Belgian Randomized Lung Cancer Screening Trial (with the Dutch acronym NELSON), the large scale screening of patients using Computed Tomography (CT) is now being considered for roll-out by national health organisations. For example, in some areas of the UK, the National Health Service (NHS) is currently enrolling over 55s who are ex-/current smokers for the 'Lung Health Check' program. In the program, those people with abnormally low lung function, say as assessed by spirometry, receive a CT scan. A CT scan is performed by a machine that analyses how much X-Rays are absorbed by the body when emitted from different angles to generate the CT, which is a three-dimensional (3D) reconstruction of the different tissues of the patient. The CT can also be referred to as a medical image, although this term is broader, in that it can also refer to images generated by other scanners, such as Magnetic Resonance Imaging (MRI), Positron Emission Tomography (PET), which are also sometimes used to aid in diagnosing lung cancer. In addition to screening programs, CT scans are often taken of the chest to check for broken bones or investigate the causes of the symptoms of disease, such as a persistent cough, shortness of breath, chest pain or fever. In addition to any other diseases such as Bronchiectasis or Chronic Obstructive Pulmonary Disease (COPD), the CT is also examined to check for lung nodules. Patients in whom suspicious lung nodules are identified then undergo a biopsy or follow-up imaging, in order to check whether the lung nodules are cancerous.

The increasing number of chest CTs that need to be examined for suspicious lung nodules is a challenge because it relies on each CT being manually assessed by an expert radiologist. To assist in the efficient and accurate examination of CTs, Computer Aided Diagnosis (CADx) devices can be used to aid in the diagnosis of detected abnormalities. CADx devices typically operate by relying on the user to identify abnormalities within the image for analysis, and then performing a series of mathematical operations on an array of intensities at the location of the abnormalities. For example, if a radiologist has identified a lung nodule in a CT scan, the CADx device can provide a score that is indicative of a risk of malignancy. The score is computed by a component of the CADx device, referred to hereinafter as the CADx system that may be a part of a machine that generates the score. That score indicates a risk or likelihood of disease, or its absence. An example of a commercial CADx device is the Transpara™ product from Screenpoint™ for breast cancer characterisation from X-Ray mammograms.

There are many examples of such CADx devices proposed within the academic literature. However, very few systems are available commercially, and hence used in clinical practice. This discrepancy is indicative of the difficulties in deploying practical systems with the known approaches. In the field of medical imaging, a variety of technologies can be used to investigate biological processes and anatomy. The following examples are types of scan that may be used to provide medical images: X-Ray; Computed Tomography (CT); Ultrasound (US); Magnetic Resonance Imaging (MRI); Single Photon Emission Tomography (SPECT); and Positron Emission Tomography (PET). Each type of scan is referred to as an "imaging modality".

Typically, a scan provides a "dataset". The dataset comprises digital information about the value of a variable at each of a plurality of spatial locations in either a two-dimensional or (more typically) a three-dimensional space. As a specific example, a CT scan may provide images of the chest of a patient. Such a CT scan might, as a more specific example, show lung nodules in the chest.

Computer Aided Detection (CADe) systems serve to assist clinicians in assessing the medical images. CADe systems need to provide a clinician with standardised, objective and repeatable information. The information typically relates to particular anatomical regions, including both normal tissue and lesions, within a person. CADe systems may be used as a so-called 'Second Reader' system. Second Reader Systems are based on an approach whereby a radiologist first looks at an image resulting from a scan, for example a mammogram. The radiologist will then, based on training and experience, identify areas of the scan where the radiologist considers that there may need to be a further investigation, for example a biopsy. However, the radiologist can then consider the CADe findings. Those findings might involve a display to highlight any additional suspicious regions on the mammogram. The radiologist will then, based on training and experience, look at those further areas of the scan. The CADe system is thereby performing a second look at the scan. The results of the second look at the scan may be that the radiologist will be directed to areas of the scan that he/she had overlooked. In this way, CADe systems are designed to reduce 'false negatives', which are also termed 'missed findings'. Thus CADe systems perform a support role to clinicians.

Computer Aided Diagnosis (CADx) systems are a related technology to CADe. CADx systems attempt to solve a different problem and relate generally to risk assessment. Instead of focussing on potentially missed findings as in CADe, they try to assist the user to classify findings correctly, either as malignant or benign in the case of potentially cancerous lesions. They rely on the user to identify abnormalities, but then typically provide a score that is indicative of the risk of malignancy. There are many examples of such CADx systems proposed within the academic literature. However, few systems are available commercially, and hence used in clinical practice. This discrepancy is indicative of the difficulties in deploying practical systems with the known approaches. The output of known CADx systems is typically some kind of score. That score indicates the risk or likelihood of disease, or its absence. An example of a commercial CADx system is the 'Transpara™' product from 'Screenpoint™'. There are many non-clinical CADx systems in the academic literature.

The score produced by a CADx system is usually the output of a statistical prediction model, for example a machine learning model, derived from relevant clinical data. Typically, this process involves identifying a set of predictors, i.e. independent variables that can be used to predict an outcome, and finding a mathematical formulation that combines them, for example by computing a weighted sum, such that its output informs on the likelihood of a particular outcome, e.g. a disease risk score. For example, in the scenario of predicting the risk that a pulmonary nodule found in a medical image is malignant, a classical statistical model could combine predictors such as the size of the nodule, appearance of the nodule, location of the nodule in the lung, and patient's characteristics such as age and smoking history in order to estimate a malignancy score. Example of models used in clinical practice to predict the risk of malignancy in pulmonary nodules include the Brock [1] and the Mayo [2] models. The predictors used in clinically used models such as Brock [1] and Mayo [2] come from the relevant clinical literature and are widely acknowledged to inform on lung cancer risk. Predictors that are currently used as inputs to models used to diagnose diseases such as lung cancer are referred to as known predictors. Prediction models are derived to provide optimal results over entire populations of patients. However, doctors make decisions about individual patients, each of whom is unique. Hence doctors value the ability to explain the reasoning of a model in arriving at a given score. When a prediction model is built around simple combinations of known predictors, it can be straightforward for the clinicians to understand the role that each known predictor plays in reaching a given score that the model outputs. A simplistic example for the case of the malignancy of pulmonary nodules is as follows: a model that combines the known predictors of nodule size and the smoking history in units of pack-years could take the form:

$$\text{LungMalignancyScore} = w_1 * \text{NoduleSize} + w_2 * \text{PackYears},$$

where the predictor weights $w_1$ and $w_2$ are determined from the data, and pack-years is the product of the number of packs smoked per day and the number of years the patient was a smoker. Here, if a patient with a nodule is not a smoker (i.e. pack-years is 0), it is clear to the clinician using the simplistic model that the malignancy score obtained is a consequence of the nodule size alone. Furthermore, the clinician can be sure that other known predictors such as the patient's history of cancer played no role in the score as it was not considered in this simplistic model. Models used in clinical practice such as Brock [1] and Mayo [2] use several more known predictors but the contribution each known predictor makes to the score that the model outputs is easily ascertained by simply looking at the equation for the model. If a model is explicable it is easier for clinicians to evaluate the efficacy of the model in supporting their decisions in individual cases, and hence decide how much credence to give the score in their clinical decision.

Nevertheless, using a simple model can come at a cost. If enough data is available, more complex models can be better at finding and exploiting relevant patterns in the data, giving them higher predictive power. However, the greater predictive power often comes at the expense of being inexplicable because of the complexity of the operations the model performs.

A common example of a class of inexplicable models is that of deep neural networks (DNN). DNNs are a type of complex model used in many domains due to their best-in-class performance and the ease with which they may be adapted to new problems. DNNs excel when they operate directly on raw data (e.g. pixels on medical images or waveforms coming from medical sensors) where they can work out which patterns in the data are good predictors for the task they perform. DNNs can also operate on structured data and can utilise a combination of several data sources. For example, a model for lung cancer prediction from images could also utilise patient related information that is not present in the images, such as clinical parameters (e.g. sex, age or whether the patient has a family history of cancer) or the outcome of related diagnostic tests (e.g. blood biomarkers). Even when the input data explicitly includes known predictors, it is not currently possible to assess their effect on a given score produced by the DNN.

Given the input data, the process of working out what patterns are relevant for fulfilling the desired prediction task is referred to as model training. Training requires a set of input data, where each datum is associated with one or more values collectively referred to as labels. For instance, in a dataset comprising of 10,000 CT images each with a cancer diagnosis indicated by the value zero or one and a smoking history indicated by a non-zero value in packyears, the diagnosis and smoking history are labels. Medical data is often inaccurate or incomplete, hence if the labels are to be used to train or evaluate a model they need to be sufficiently accurate. When labels have been verified to be accurate, they are referred to as ground-truth. During training, the model parameters are automatically adjusted by an optimization algorithm. The optimization algorithm measures how well the model performs at the task and works out what changes to the model parameters are needed to make the model perform better. The optimisation is repeated until the model performs well on another set of data that is not used for training. An example of a task is discerning benign from malignant nodules from CT images, where model performance is measured using a label for diagnosis that is supplied with the training images. The lack of direct control over model parameters, and hence the patterns that the DNN will take into account to solve the task, in combination with the level of complexity of the operations that the DNN performs to go from input to output, have led to the general concern that DNNs are inexplicable.

The predictors worked out by the model are referred to as features. When an input is presented to the model each feature responds to a particular set of patterns in the input data and outputs a value known as an activation. The model combines the feature activations using a mathematical function, for example a weighted sum, to produce the model output, for instance a risk score. Since the features are obtained automatically it is difficult to assess the role, if any, of known predictors within a DNN score. In fact, the DNN could be using certain patterns in the raw data that do not correspond to any known predictors for the task at hand. For example, a DNN predicting malignancy of a lung nodule could find that a specific complex arrangement of pixel intensities in the image is more likely to occur in malignant nodules, and hence use it as a malignancy predictor. If it is not possible for a clinician to understand what aspects of the input caused the model to predict a certain risk score, or judge whether the model has failed, then it may be difficult for clinicians to trust such models enough to use them in practice, even when they have been proven to improve the overall diagnostic accuracy.

General purpose techniques for explaining the output of DNNs have been emerging from academic research, but they have largely focused on highlighting the segments of the raw input data which had the highest influence on a given output (e.g. visual attribution or network saliency maps [3]). However, this attribution information does not necessarily explain why the risk is deemed high or low. In the case of a nodule in a CT image which is predicted to have a high risk of being malignant, such techniques would not be able to express the clinical concepts that doctors use for decision making, such as size and irregular density, thus they do not provide a solution for being explicable in a clinical setting. Furthermore, even if a DNN model considers the same image features as clinicians, the way the features are encoded within the model does not currently allow the output of the model to be explained.

REFERENCES

[1] McWilliams A, Tammemagi M C, Mayo J R, et al. Probability of cancer in pulmonary nodules detected on first screening CT. N Engl J Med. 2013 Sep. 5;369(10): 910.
[2] Swensen S J, Silverstein M D, Ilstrup D M, et. al. The probability of malignancy in solitary pulmonary nodules. Application to small radiologically indeterminate nodules. *Arch Intern Med.* 1997 Apr. 28;157(8):849-55.
[3] M. D. Zeiler and R. Fergus. Visualizing and understanding convolutional networks. In European conference on computer vision, pages 818-833. Springer, 201

SUMMARY OF THE INVENTION

Accordingly, the invention seeks to mitigate, alleviate or eliminate one or more of the abovementioned disadvantages singly or in any combination.

According to the invention there is provided a method for providing a lung disease risk measure in a Computer Aided Diagnosis system comprising: receiving an input comprising at least one input image showing all or part of the lungs of a patient; analysing the input to identify a feature descriptor comprised of at least one feature group, where each feature group comprises at least one feature computed from the input image; calculating a score explanation factor for each feature group, and an overall disease risk score for the patient's risk of lung disease from the feature descriptor; outputting the overall disease score risk score and a corresponding score explanation factor for each feature group.

In a preferred embodiment of the invention, the input further comprises one of more of: biomarkers for the patient or clinical parameters for the patient. Preferably, the biomarkers and clinical parameters comprise: patient age, patient sex, family and clinical history, results of blood tests, results of lung function tests.

In an embodiment of the invention the risk score explanation factor is related one or more of tumour size, location and appearance.

Further preferably, each at least one feature group comprises a plurality of features for that feature group.

In an embodiment of the invention the CADx system uses a neural network. Preferably, the neural network is a convolutional neural network.

In a further embodiment of the invention the overall disease risk score is calculated using a mapping function on the feature descriptor.

According to the invention there is also provided a computer aided diagnosis lung disease risk measure system comprising: an input circuit configured to receive at least one input image showing all or part of the lungs of a patient; an analysis and score circuit configured to: analyse the at least one input image to identify a feature descriptor comprised of at least one feature group, where each feature group comprises at least one feature derived from the input image; calculate a score explanation factor for each feature group and an overall disease risk score for the patient's risk of lung disease from the feature descriptor; an output circuit to output the overall disease score risk score and a corresponding score explanation factor for each feature group. Preferably, the analysis and score circuit further comprises a feature encoder to receive the input image and identify the feature descriptor.

In an embodiment of the invention, the score explanation factor is calculated by applying a mapping function to the feature descriptor.

In an embodiment of the invention there is also provided a method for training a Computer Aided Diagnosis system as described above comprising the steps of: providing a machine learning model to be trained using multiple inputs; providing an input of at least one input image and at least one ground truth label to the machine learning model of the CADx system; optimising the input to obtain a prediction output comprising a risk score and an estimate of known predictors; updating the machine learning model based on the prediction output and repeating the steps until all of the multiple inputs have been provided to the machine learning model.

Preferably, the prediction output further comprises a score explanation factor.

In an embodiment of the invention, the input comprises at least one input image and at least two ground truth labels. Preferably, the ground truth label includes at least one of a ground truth diagnosis and information on known lung disease predictors.

In a further embodiment of the invention a difference between the estimate of known predictors, the risk score and the ground truth labels is determined using a loss function. Preferably, the loss function includes a term to penalise the correlation between feature groups. Further preferably, the loss function is:

$$L = \Sigma_{x \in \{u; A; B; \ldots K\}} E_x(\hat{F}_x, F_x) + \lambda \Sigma_{z \in \{A; B; \ldots K\} \setminus \{x\}} R(v_x, v_z).$$

In an embodiment of the invention, the loss function also includes a further loss term, to enforce non-zero contributions for known features to match clinical knowledge.

The invention is centred around the idea of decomposing the risk score produced by an inexplicable machine learning model into a set of contributions made by known predictors. In the case of lung cancer risk of a pulmonary nodule, some examples of known predictors of malignancy include nodule size, nodule growth, homogeneity of the nodule density, regularity of the nodule boundary, retraction of the lung pleura near the nodule, convergence of lung vasculature into the nodule, and calcifications, fatty tissue or cavities in the nodule, amongst others. The contributions that the known risk predictors make towards the risk score of the model can be provided to the clinician as an explanation of how the model arrived at that score. This can allow clinicians not only to understand the risk score through an explanation in familiar and relevant terms but, crucially, to judge the accuracy of the output of the model, thus enabling a mechanism for quality assurance.

It is important to note that in order to obtain a useful explanation of the risk score, the ability to calculate the contribution of each predictor to the score needs to be built into the machine learning model at training time. A "built-in explanation" differs from simply having a collection of machine learning models that operate in parallel: for example, a super-model that comprises of a model for disease risk and a model for detecting each of the known predictors that make up the explanation of the score in clinical terms. Independent parallel models that output known predictors that operate independently of the risk model cannot be considered a direct explanation of the risk score, as the models have not been trained in a manner that allows their contribution to risk score to be calculated.

BRIEF DESCRIPTION OF THE DRAWINGS

Further details, aspects and embodiments of the invention will be described, by way of example only, with reference to the drawings. In the drawings, like reference numbers are used to identify like or functionally similar elements. Elements in the figures are illustrated for simplicity and clarity and have not necessarily been drawn to scale.

DETAILED DESCRIPTION

Figure 1:
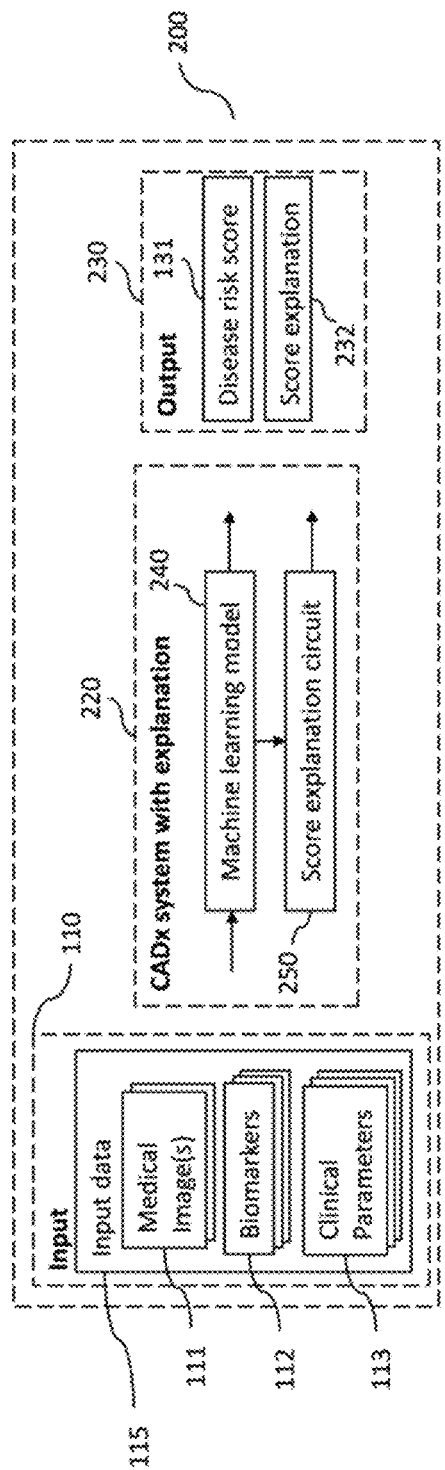
FIG. 1 illustrates a CADx system according to an embodiment of the invention.

FIG. 1 illustrates a device (200) with a CADx system with explanation (220), which contains the subject of this invention. A set of input data (115) for a patient is provided to the CADx system with explanation through an input circuit (110). The patient input data (115) consists of at least one medical image (111), as well as further optional information from other previously performed diagnostic tests on the patient that are biomarkers such as such as lung function or blood tests (112), and optionally clinical parameters from patient information relevant to diagnosing the lung disease such as age or sex (113). The CADx system with explanation (220) processes the input data (115) using a machine learning model (240). The output from the CADx system is a disease risk score (131) with a disease risk explanation (232).

In this embodiment of the invention the CADx system with explanation (220) includes a machine learning model (240) and a score explanation circuit (250). The score explanation circuit works alongside the machine learning model (240) by capturing the patterns that are being considered by the machine learning model (240) when producing the disease risk score (131), and then explaining the patterns using clinically known predictors. As previously described, patterns refers to certain arrangements of the values in the input data whose presence is informative in determining whether a nodule shown in a medical image is malignant or benign.

The output of the novel CADx system (230) of this invention, consists not only of the risk score for the patient for the disease (131) as determined from the input data, but also the decomposition of the risk score for that patient into a contribution that each known predictor made to the risk score, which is referred to as a score explanation (232).

Example Implementation Diagram of the Cadx System with Explanation

Figure 2:
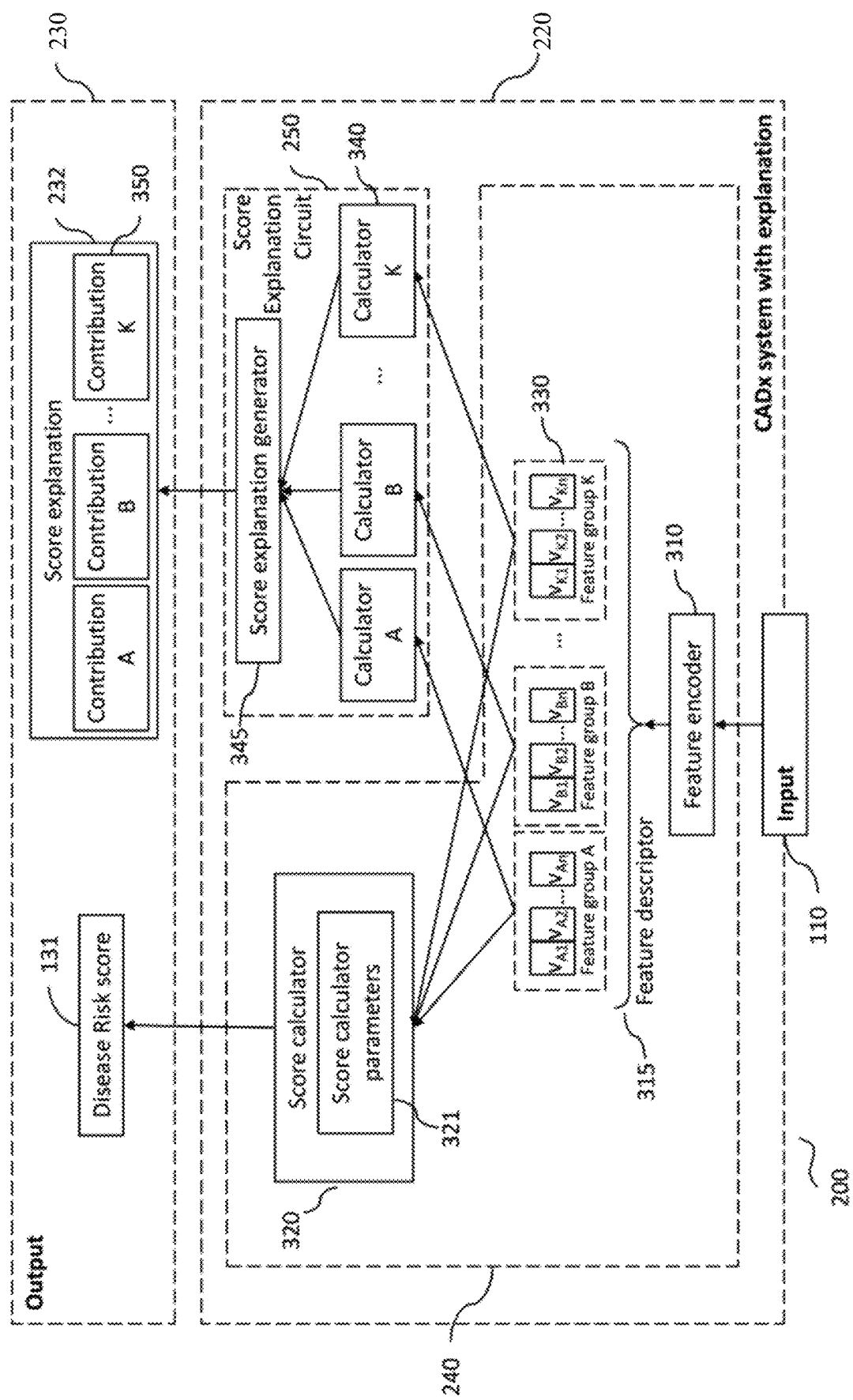
FIG. 2 show a more detailed example implementation of a CADx system of FIG. 2.

An example implementation of a CADx system with explanation relies on structuring the machine learning model (240) and using a loss function during training of the machine learning model, such that each feature in the model is correlated with at most one known predictor. Each group of features that are correlated with a known predictor are collectively referred as a feature group. FIG. 2 shows Feature groups A, B, . . . K that are composed of feature elements $V_{A1}, V_{A2}, \ldots V_{AN}; V_{B1}, V_{B2}, V_{BN}, \ldots V_{K1}, V_{K2}, \ldots V_{KN}$. (330) Feature elements are unique to each feature group and cannot be duplicated between feature groups. For example, a feature group may contain features related to size, spiculation or other features.

The features that are used to calculate the risk score (131) but that are not correlated with any known predictors are referred to as features for unknown predictors and are collectively known the feature group for unknown predictors. All feature groups whether for known predictors or unknown predictors are used to calculate the model score. After training of the machine learning model is complete, when the model is presented with input data, the level of activation for a feature reflects to what extent that feature or its antithesis is present in the input data. The level of activation of a feature group relative to the others allows the calculation of the contribution of that feature group towards the risk score.

In an embodiment of the invention, the features in a feature group (330) for unknown predictors are activated by the input (110) and contribute to the output (320), but are independent of the other feature groups. Any predictor that is used in the explanation is the product of patterns that appear in the images, whether the patterns correlate to known predictors or not. That is, for some of the features being used by the neural network, they correlate to what doctors in the area normally use as predictors for the disease. Other features might not correlate to anything that is known in the literature. For example, the model may have 3 predictors: one correlated to nodule size, one aligned to nodule boundary regularity, and an unknown predictor. Every pattern the network finds useful, it will use it for its prediction. However, we "force" the network to make one of those patterns correlate to size, one to nodule boundary regularity, and anything else it wants to consider would be captured by the group of unknown predictors.

The feature groups are selected to correlate with at most one known predictor by carefully choosing an appropriate loss function. Initially all features in all feature groups are assumed to have non-zero correlation with all known predictors, but during training the scaled derivative of the loss function with respect to the model parameters is subtracted from the current model parameters. The modification of the model parameters causes the correlations to decrease. The loss function and scaling are chosen such that features eventually have a non-zero correlation for at most one known predictor. In practice, because of how model optimisation is performed, "non-zero" should be taken to mean "not close to zero", e.g. correlations of less than one in ten thousand are treated as being zero for practical purposes.

A more detailed example implementation of a CADx system with explanation (220) is shown in FIG. 2. At the core of the CADx system, there is a predictive machine learning model (240), which in a preferred embodiment of the invention typically consists of i) a feature encoder (310) that produces a feature descriptor v (315), and ii) a score computation circuit (320), with a set of score calculation parameters $w_s$ (321), which transforms the feature descriptor into the disease risk score (131) which is output from the circuit.

The feature descriptor (315) is an intermediate mathematical representation which usually takes the form of a high-dimensional vector v, where every entry in the feature descriptor encodes the strength with which some pattern is present in the input data (115). The strength is typically a transformed weighted sum of values within the input data. Transformations may vary but are usually a regularised linear unit where negative values are set to zero. The parameters used to transform the input into a feature descriptor are automatically generated when the model is trained. As an example, the score calculator (320) can transform the feature descriptor (315) into the disease risk score (131) through a mapping function of the following form:

$$\text{score} = f(v; w_s) \quad (2.1)$$

The score explanation circuit (250) in this example uses the output of the feature descriptor (315), which has been specially designed and trained such that its elements can be grouped. The term element refers to a single activation, itself uniquely associated with a feature, within a feature group. In the feature descriptor (315) each entry has the symbol $v_{xy}$, where the subscript x indicates the group the feature is a member of, and y indicates the index of the feature activation within the group. The idea behind the grouping is that a group can be designed to respond to a specific high-level concept of interest such as a known predictor that is known to be associated with the disease that the CADx system is assessing, while being insensitive to the patterns that the rest of the groups respond to. For example, in a CADx system for lung cancer risk assessment, elements in the feature group K (330) can be responsible for encoding the known predictor "smoothness of the nodule boundary", or "size of the nodule", etc. A feature in a particular feature group does not need to be correlated with any known predictor of the disease. For example, a feature such as the appearance of two blood vessels on one side of a nodules and striations at the margin of the other side of the nodule could be important for predicting malignancy but has never before been described in the clinical literature. Hence, the model does not need to compromise its predictive accuracy by being restricted to only being activated by features associated with known predictors.

Preferably, the training method allows the feature descriptor (315) of the machine learning model (240) in the CADx system to be split into independent feature groups, each exclusively associated with a predictor.

Each feature activation and hence each feature group is induced by the training procedure to belong to at most one known predictor. Feature groups consist of at least one feature activation. A preferred embodiment of the invention requires at least two feature groups, one of which may be the feature group for unknown predictors.

Given grouped features (330) and the parameters, $w_{s \in k}$, (321) of the score calculator (320), the score explanation circuit (250) can use feature group calculators (340) in order to map the activity of a feature group into a value indicative of the proportion of contribution made by each known predictor to the disease risk score (350) and the total contribution of unknown predictors.

For example, the feature group calculator K (340) will compute a value of strength for the predictor encoded by the feature group K (330). The score explanation circuit 250 has calculators A, B . . . K (340) corresponding to each of the feature groups (330) in the feature descriptor (315). Then, the score explanation generator (345) will use the contribution of each known predictor and optionally also the total contribution of unknown predictors to the risk score to assemble the explanation of the score (232) to provide to the user alongside the disease risk score (131). Hereafter, the term predictor refers either to a single known predictor or the combination of unknown predictors. The score explanation contains the information related to the contribution of each of the predictor, e.g. the contribution of predictor K (350). In one example of the CADx system with explanation (220) the feature group calculators (e.g. 340) compute the contribution of the corresponding predictor using the following equation:

$$\text{contribution}_k = w_{s \in k}^T \cdot v_k / w_s^T \cdot v \quad (2.2)$$

Where $w_{s \in k}$ and $v_k$ are respectively the subsets of $w_s$ and v which account for predictor K in the computation of the disease risk score (131).

In a preferred embodiment of the invention, the score explanation circuit (250) decomposes a CADx score from a machine learning model (240) into at least two contributions by two predictors of a disease. At least one of the contributions should be for a known predictor, i.e. a parameter, such as nodule size, that is known by clinicians to be correlated with the presence or absence of the disease. The model comprises of features that produce an activation, i.e. a scalar value produced in response to the input. Each feature is associated with at most one known predictor, i.e. its activation is used to produce an estimate of the known predictor when the model is being trained. Features (if any) that are not associated to a known predictor are collectively known as features for unknown predictors. Optionally, one of the contributions may comprise of the total contribution of features for unknown predictors with the remaining contributions coming from known predictors. The set of contributions is collectively known as the explanation of the CADx score In an alternative embodiment of the invention, the score explanation circuit (250) decomposes a CADx score from a machine learning model (240) into at least two contributions by two predictors of a disease and the features are projected into a new space to form a set of feature projections. At least two sets of feature projections are associated with two known predictors, i.e. their activation is used to produce an estimate of the known predictor when the model is being trained. Features (if any) that are not associated to a known predictor are collectively known as features for unknown predictors. Optionally, one of the contributions may comprise of the total contribution of features for unknown predictors with the remaining contributions coming from known predictors.

Figure 3:
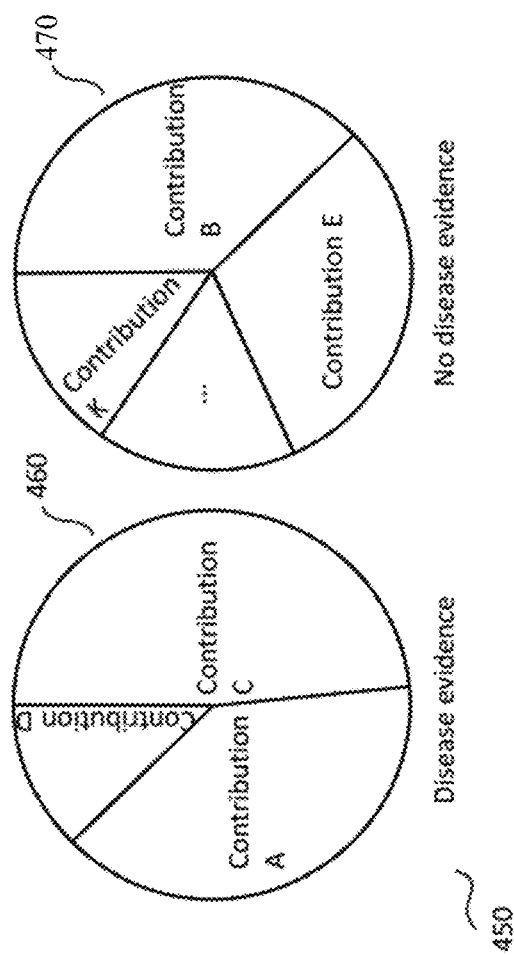
FIG. 3 shows examples of score explanation according to an embodiment of the invention.
Figure 3:
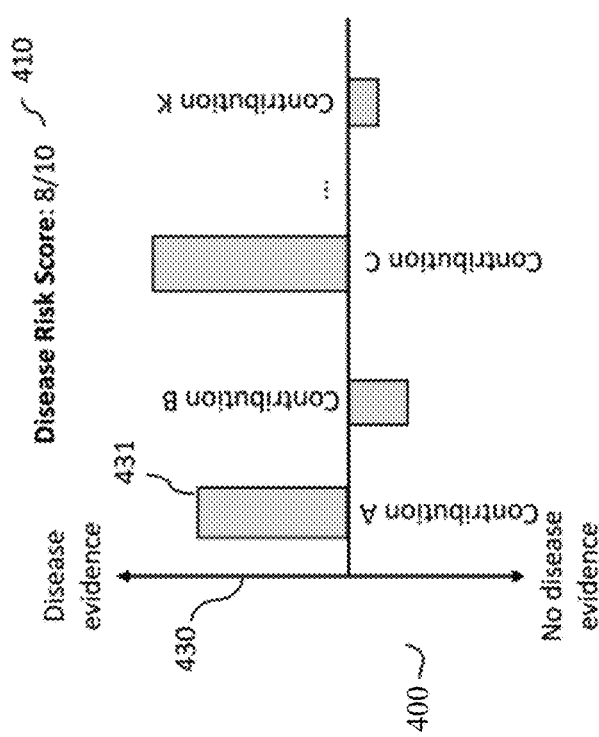

The score explanation generator (345) is a general circuit and its output can be provided to the user in many different ways. For example, in one embodiment of the invention, the score explanation can be given in the form of graphics, some examples of which are shown in FIG. 3. For instance, in the form 400, the components of a given disease risk score (410) could be shown as a set of bars along a disease evidence axis (430) such that the height (431) of the bar for each predictors would add up to the disease risk score (410). Therefore, the user can see how the contributions of individual predictors can serve to both increase or decrease the risk score. For example, the user can be shown how nodule size and irregular appearance of its boundary can increase the score, while a homogeneous nodule density can decrease it. The additional total contribution can also be shown for unknown predictors that contribute to the score but are independent of the known clinical predictors such as size, other factors that describe the appearance of the nodule such as spiculation, attenuation, lobulation and the presence of calcification, and the location of the nodule in the lung. In another example of a graphical score explanation (450), the relative contribution of the predictors towards a hypothesis that the disease is present (460) can be shown separately to predictors contributing to a hypothesis that the disease is not present (470). Alternatively, the score explanation could be provided the form of a predefined structured report using the output of the score explanation generator (345). Likewise, the score explanation can be in the form of free text, in which case the score explanation generator (345) can provide its output to a generator of natural language which converts the disease risk score and predictors into a text-based report, for example, in the style of a radiological report in the case of a CADx system for lung cancer risk.

Overview of how to Train a Model for a CADx System with Explanation

Designing and training a machine learning model (e.g. a neural network) that has the property of grouping elements of the feature descriptor (315) into the different feature groups (330) in a way that they can be used for the risk score explanation, can be done in different ways and with varying degrees of how specific each feature group is to its corresponding predictor. An approach which strongly enforces the specificity of the feature groups, would at least rely on the training data being labelled, not only with the known disease diagnosis of the cases in the training data, but also with the information regarding the presence (or lack thereof) of the predictors that the CADx system will use in the score explanation. Each predictor would then match to one of the K pre-defined groups (330) of elements in the feature descriptor (315), and the training objective function of the optimization algorithm would include an error term to enforce that each feature group consists of features that enable the accurate estimation for the predictor (if it is a known predictor) that is associated with it, while being uncorrelated with the remaining predictors (whether known a known predictor or the total contribution of unknown predictors), thus making the feature group specific to a single predictor. A typical error term will be a function of the difference between the predicted value and a ground-truth label.

Example of a Model Training Process

Figure 4:
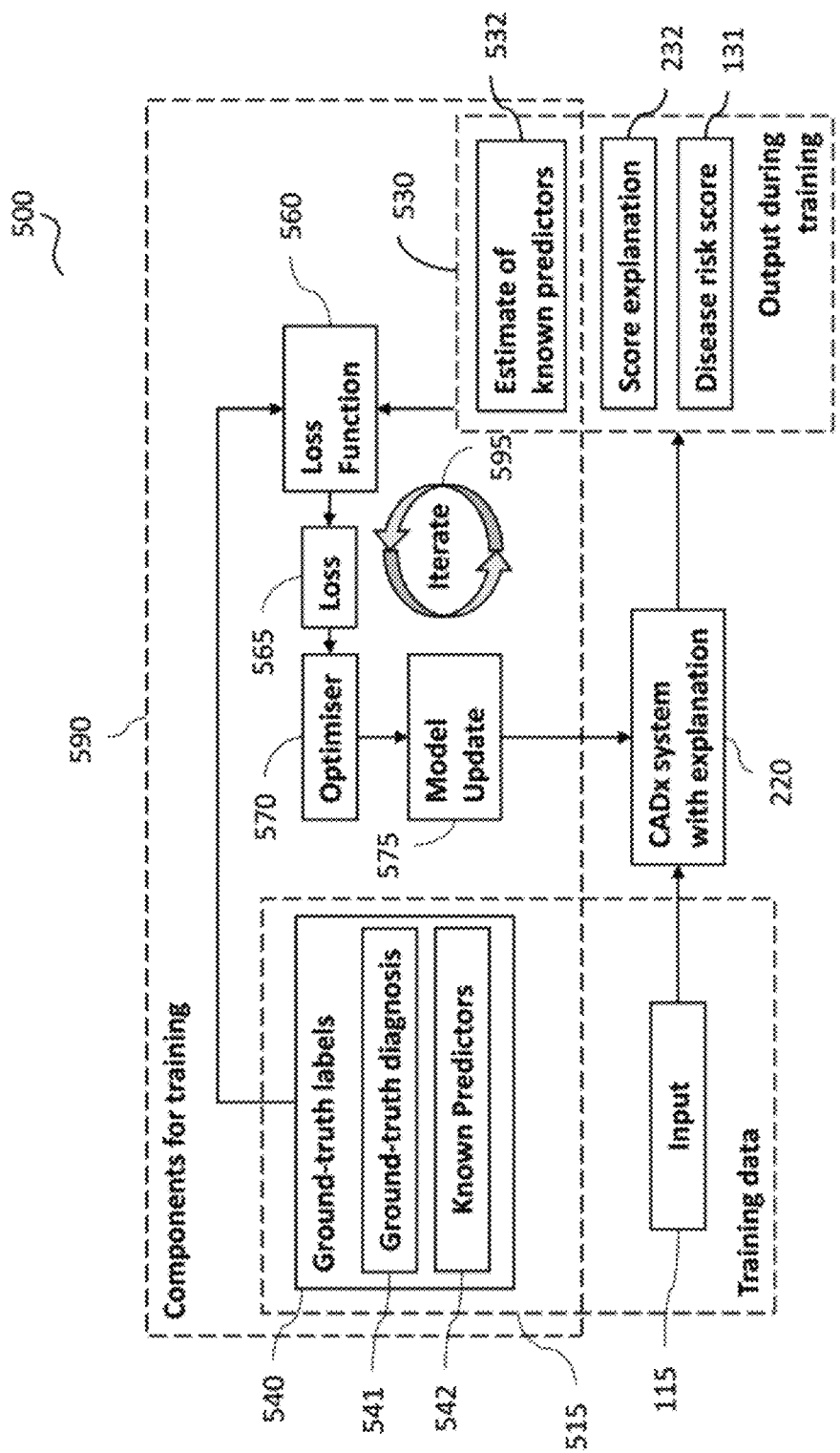
FIG. 4 shows an example of the training process for the CADx system according to an embodiment of the invention.
Figure 5:
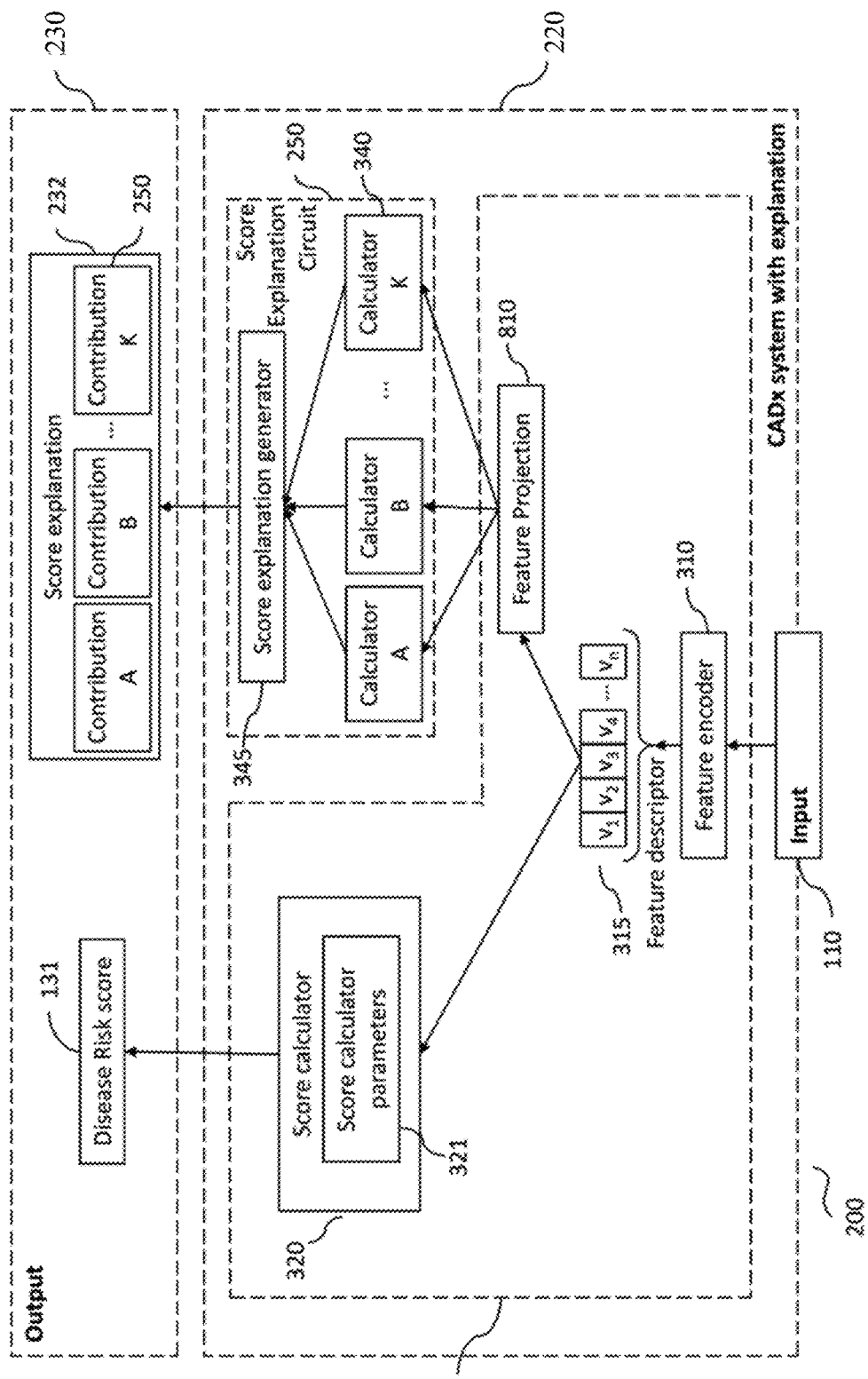
FIG. 5 shows an example of an embodiment of the CADx system of this invention.

FIG. 4 shows illustrates an example of the training process of a model for the CADx system with explanation (220) where labels for known predictors are available as input training data for training the model.

In accordance with some examples of the invention, the model parameters for the machine learning model (240) and score explanation circuit (250) need to be obtained using a training algorithm in order to generate a useful predictive output (230) from the input data (115). The training process (500) relies on additional training components (590), including ground-truth labels (540) for each data sample in the training dataset (i.e. the set of input data (115) used during the model training). For an input data set, the ground-truth labels (540) may consist of the ground-truth diagnosis of the disease (541), as well as information on the known predictors (542). The input data (115) and the corresponding input ground-truth labels (540) are provided together by the input circuit (515) to the optimisation algorithm.

In some examples of the invention, the training of the CADx system with explanation system (220) may entail repeatedly presenting one or more sets of input data (115) to the CADx system with explanation (220), in order to obtain a prediction output (530) comprising of both a risk score (131) and an estimate of the known predictors (532). In some examples of the invention, the difference between the estimate of the known predictor (532), the risk score and the corresponding ground-truth labels (540) associated with the corresponding input data set (115) may be computed using a loss function (560).

In some examples of the invention, the loss function is designed such that the training of the model penalises the existence of correlation between different feature groups in the feature descriptor (315). An example of such loss function is shown in equation (4.1):

Example Loss Function:

$$L = \Sigma_{x \in \{u;A;B;\ldots K\}} E_x(\hat{F}_x, F_x) + \lambda \Sigma_{z \in \{A;B;\ldots K\}\setminus\{x\}} R(v_x, v_z) \quad (4.1),$$

where the loss function, L, computes the sum of prediction errors, E, with the risk particular prediction error being indicated by x, and the sum of the correlations, R, for each pair of feature groups indicated by x and z. A prediction error, $E_x$, is calculated from a set of predictions, $\hat{F}_x$, that are computed from a set of inputs, and a set of ground truths, $F_x$, associated with the inputs. The predictions and groundtruths are for the risk score, when x=u, and each of the known factors, when x∈{A; B; . . . K}. $E_x$ could be a negative cross-entropy function, a sum of square differences, a sum of absolute differences, or another loss function as those skilled in the art will appreciate. $v_x$ and $v_z$ each indicate a first and a second feature group. The correlation loss weight, λ, controls the relative weight of R in the loss function.

In some examples of the invention, the loss function may also include a further loss term, I(c), to enforce non-zero contributions for known features to match clinical knowledge. An example of such loss function is shown in equation (4.2):

$$L = \Sigma_{x \in \{u;A;B;\ldots K\}} E_x(\hat{F}_x, F_x) + \lambda \Sigma_{z \in \{u;A;B;\ldots K\}\setminus\{x\}} R(v_x, v_z) + l(c) \quad (4.2)$$

For example, nodule size is known to be a strong predictor of malignancy, so I(c) can be set to $$-\Sigma_{x \in size\text{-}feature\text{-}group} |v_x|$$

to features that are associated with nodule size are always considered in the risk score.

In some embodiments of the invention, a modification to the loss function in the training algorithm where some correlation between the known predictors is allowed so that it is not necessary for all the training data to have a label for every known predictor.

In some examples of the invention, an optimisation algorithm (570) may be used to calculate a change in the model parameters, referred to as a model update (575) that would reduce the loss (565) output by the loss function (560). Following a model update, the examples can again be presented as an input to the model in order to compute a new update. Each cycle of calculating a loss (565), calculating a model update (575) and updating the model is referred to as an iteration (595).

In some examples of the invention, the loss (565) is also computed for a second set of input data and corresponding input ground-truth labels, but where model updates are not performed. This is referred to as the validation set. The validation set can be used to decide when to terminate a training process, for example when the loss (565) for the validation set no longer decreases. The second set of data is randomly selected from the available data with the constraint that there is no overlap between the training data and the validation data.

After the training of the model is complete, the model can estimate the risk score (131) and score explanation (232) from input data (115) without the need for any of the components for training (590). Therefore, these components for training (590) can be discarded after the training process has completed.

Example of a Simplified Process of Model Training

The correlation loss in equation (4.2), controls to what extent specific feature groups correlate to more than one factor, and hence induces the features to align to at most one predictor. However, such a penalty is not mandatory, and removing it can avoid needing labels for every known predictor available for every training input, leading to a simplified training process. Allowing incomplete labelling can be convenient, even if it results in approximated versions of the score explanation in terms of its factors, where the features are only approximately correlated to known predictors without being highly specific to them. For example, the model can be trained without the requirement to explain the score in terms of known predictors (i.e. the loss function is (4.1) instead of (4.2)). Then, a post-training analysis of the model can reveal correlations between elements in the feature descriptor and risk predictors As an example of this approach, the post training analysis could consist of identifying the principle components of the model's feature descriptor (315), by using the Principal Component Analysis (PCA) technique:

$$P = PCA(X_s) \qquad (4.3)$$

Where $X_s$ contains the feature descriptor (315) vector for a selection of sample inputs (115), and P is a projection matrix which can be used to project the feature descriptor (315) of any individual sample $x_i$ onto a set of principle components, each of which is a single value computed from a weighted sum of the elements of the feature descriptor:

$$\hat{x}_i = P \cdot x_i \qquad (4.4)$$

Where $x_i$ is the feature descriptor (315). Here, the score explanation is produced from the projected version of the feature descriptor (610), $\hat{x}_i$.

However, the projected features need to be linked to the known risk predictors. The linking to the known predictors can be done qualitatively by estimating a correlation between the principle components and the known predictors. For example, a set of example images which capture the variability for each of the projected features identified through PCA can be inspected by an expert who can qualitatively estimate how well each projected feature correlates to one or more of the known predictors, and hence provide a clinical term (or combination of terms) for each of them. Similarly to before, projected features which do not show any relation to known predictors are referred to "projected features for unknown predictors".

Once the relationship between projected features and known and unknown predictors has been established, the explanation can be produced as before, but where the contribution of predictor k towards the output score, similar to (2.2), is now:

$$\text{contribution}_k = w_s^T \cdot P_k^T \cdot P_k \cdot v / w_s^T \cdot v \qquad (4.5)$$

The explanation in terms of the features discovered post-training can still suffice to produce a satisfactory score explanation even when the factors considered by the model are only weakly correlated with the known risk predictors. An example of an unsatisfactory score explanation would be when a model incorrectly considers a nodule's margins to be "ragged" or spiculated as a result of being near a region with many vessel branches in the lung. If spiculation is the primary cause for the nodule incorrectly receiving a high score indicating likely malignancy, a clinician assessing the nodule can identify this and disregard the model's score. Where the score explanation did not contradict the clinician's intuition, the result is deemed satisfactory, with the advantage that the known predictor and its contribution to the score has been calculated in a repeatable and objective manner.

Example of the Physical Implementation of the Model

Figure 6:
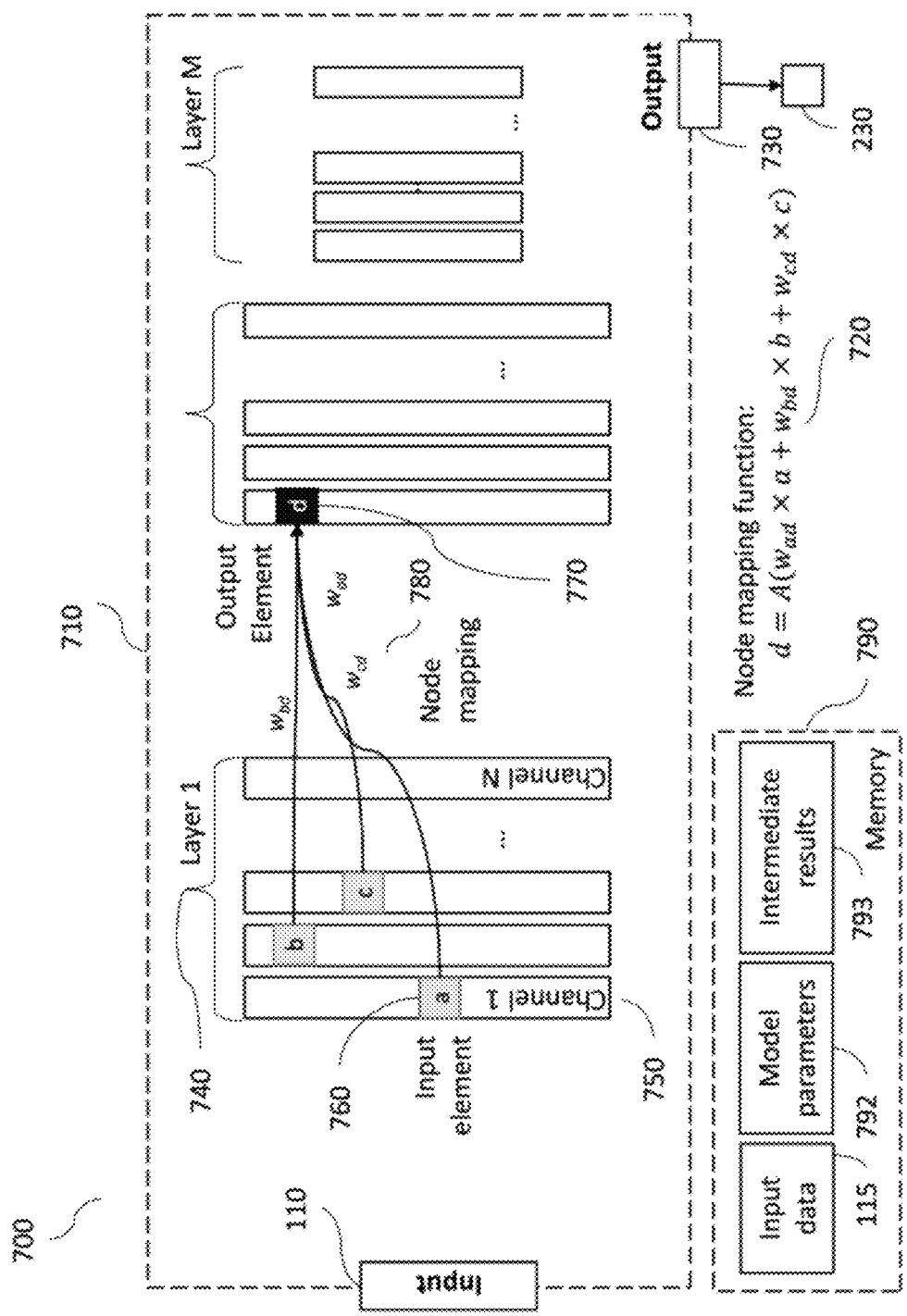
FIG. 6 shows a CADx in an embodiment of the invention that uses a neural network.

Referring now to FIG. 6, the CADx system with explanation (220) may be, for example, the illustrated neural network (710), according to examples of the present invention. In some examples, the CADx system with explanation (220) may comprise a neural network (710), which applies a series of node mappings (780) to the input data provided by the input circuit (110), which ultimately resolves into an output (730) consisting of one or more values, from which at least one of the values is used by the CADx system (220), for example a risk score (131) and explanation (232) in the output circuit (230) of FIG. 1. The input layer may, for example, include the values of the input medical image (111) or for example a value representing the patient's age or whether the patient had a family history of cancer.

The example neural network (710) comprises a consecutive sequence of network layers (e.g. layers 740), each of which consists of a series of channels (750). The channels (750) are further divided into input elements (760). In this example, each input element (760) stores a single value. Some (or all) input elements (760) in an earlier layer are connected to the elements in a later layer by node mappings (780), each with an associated weight. The collection of weights in the node mappings (780), together, form the model parameters (792). For each node mapping (780), the elements in the earlier layer are referred to as input elements (760) and the elements in the output layer are referred to as the output elements (770). An element may be an input element to more than one node mapping, but an element is only ever the output of one node mapping function (720).

In order to calculate the output (730) of the neural network (710) the system first considers the input data as the earlier layer. The layer(s) to which the earlier layer is connected by a node mapping function (720) are considered in turn as the later layer. The value for each element in later layers is calculated using the node mapping function (720) in equation (5.1), where the values in the input elements (760) are multiplied by their associated weight in the node mapping function (720) and summed together.

$$\text{Node mapping function (720): } d = A(w_{ad} \times a + w_{bd} \times b + w_{cd} \times c) \qquad (5.1)$$

The result of the summing operation is transformed by an activation function, 'A' and stored in the output element (770). The neural network (710) now treats the previously considered later layer(s) as the earlier layer, and the layers to which they are connected as the later layers. In this manner the neural network (710) proceeds from the input layer (740) until the value(s) in the output (730) have been computed.

In some examples of the invention, the feature encoder (310), the score calculator (320) and the calculators (e.g. 340) will each correspond to particular layers within network. Typically, the layers corresponding to the feature encoder would be a set of layers from early in the network (typically from layer 1 up to almost the end of the network), whereas the score calculators and calculators would be at the end of the network (typically the final layers).

In examples of the invention, the neural network (710) may be trained using a set of input data from patients with associated ground-truth labels (540) that, say, specify the ground-truth diagnosis of the input data and the known predictors that were present in it. In some examples of the invention, the training of the neural network (710) may entail repeatedly presenting at least one input data set to the input circuit (110) of the convolutional neural network (710), in order to obtain the estimated risk score and score explanation (230) of FIG. 1, for example by following the process (500) with training components (590) analogous to those in FIG. 4. In some examples of the invention, the difference between the estimated output (230) and the ground-truth labels may be computed using a loss function, analogous to (560). In some examples of the invention, an optimisation (e.g. 570) algorithm may be used to reduce the loss, for example by measuring how much each node mapping (780) weight contributed to the loss, and using this to modify the node mapping functions (720) in such a way as to reduce the loss. Each such modification is referred to as an iteration. After enough iterations, the neural network (710) can be used to estimate a disease risk score alongside the score explanation for novel input data.

In some examples of the invention, the large number of parameters used in the neural network may require the device to include a memory (790). The memory (790) may be used to store the input data (115), the model parameters (792), and the intermediate results of the node mappings (793).

In some examples, another neural network can comprise the CADx system, which may differ from the neural network in the CADx system with explanation (220) in architecture but still operate using the same principles. Hence, while the above description of a neural network refers to the CADx system with explanation, a skilled artisan will readily appreciate that an analogous approach can be used to construct a CADx system with explanation, such as CADx system with explanation 220 in FIG. 2.

In a preferred embodiment of the invention, the training method as described above allows the feature descriptor (315) of the machine learning model (240) in the CADx system to be split into independent feature groups, each exclusively associated with a predictor.

In a further preferred embodiment of the invention the score explanation circuit (250) for decomposing a CADx score from a machine learning model (240) decomposes the CADx score into at least two contributions by two predictors of a disease, by using at least two combinations of features of the model projected into a new space.

A modification to the loss function in the training algorithm of an embodiment of the invention, where some correlation between the known predictors is allowed so that it is not necessary for all the training data to have a label for every known predictor.

Those skilled in the art will readily appreciate that the CADx system with explanation (220) can be implemented as a hardware device, a software package in a general-purpose computer, or on a firmware device such as a DSP.

This invention allows doctors to understand the reasoning by which machine learning models in Computer Aided Diagnosis systems come to a particular conclusion such as a lung cancer score for a given CT. As a result, the doctor can decide how much they trust the output of the system, how much consideration to give to its assessment.

The invention improves on the transparency of current state-of-the-art machine learning models whose best-in-class performance comes at the price of being inexplicable.

The lack of explicability in complex machine learning models is a barrier to their uptake in the clinic and reduces their value when in use because it is difficult for clinicians to assess how much credence to give the model output in their considerations when coming to a clinical decision about an individual patient.

This invention can be applied in the context where a CADx system, powered by a machine learning model, is used to assess the risk of disease from input medical data such as medical images. Specific scenarios include:

The machine learning model is part of a decision support system used by a clinician assessing the risk that a patient has a particular disease from relevant input data. The risk score is provided along with an explanation indicating the relative importance assigned to a set of known predictors that are clinically accepted as being known predictors for the risk of the disease. For example, in the case of a CADx system for lung cancer risk from pulmonary nodules, these include nodule size, density and margin. Using the explanation, the clinician can then decide whether to take the score into consideration (e.g. if they agree with the explanation) or ignore it.

The CADx system is integrated with an automated reporting system, where the risk score is written in the report accompanied by a text-based explanation of the predictors driving the given score. For example, if the CADx system is built to assess risk of lung cancer from pulmonary nodules, it can be integrated with a radiology reporting system. The CADx system could then supply its explanation for input into a text form, describing the predictors that contribute the most to the score. Thus, examples of the invention provide a CADx system that can be trained, such that it optimises performance whilst taking into account the overall clinical context. Considering the example discussed, it is not necessary to correctly estimate the malignancy of nodules of all medical images to obtain clinical and economic benefit. For instance if the CADx system classifies nodules as either malignant or benign, one aim of examples of the present invention is to maximise a number of benign nodules that are correctly classified, whilst not misclassifying any malignant nodules.

Although examples of the invention have been described with reference to the CADx system being used to assist in the interpretation of chest images and lung nodules, it is envisaged that the concepts described herein may be employed beyond this area of the human body. In other examples, it is envisaged that the concepts may be applied in any medical application where it is important to consider other aspects of the clinical context, such as economic and patient preferences, where one or more medical images are being analysed.

The present invention has been described with reference to the accompanying drawings. However, it will be appreciated that the present invention is not limited to the specific examples herein described and as illustrated in the accompanying drawings. Furthermore, because the illustrated embodiments of the present invention may for the most part, be implemented using electronic components and circuits known to those skilled in the art, details will not be explained in any greater extent than that considered necessary as illustrated above, for the understanding and appreciation of the underlying concepts of the present invention and in order not to obfuscate or distract from the teachings of the present invention.

The invention may be implemented in a computer program for running on a computer system, at least including code portions for performing steps of a method according to the invention when run on a programmable apparatus, such as a computer system or enabling a programmable apparatus to perform functions of a device or system according to the invention.

A computer program is a list of instructions such as a particular application program and/or an operating system. The computer program may for instance include one or more of: a subroutine, a function, a procedure, an object method, an object implementation, an executable application, an applet, a servlet, a source code, an object code, a shared library/dynamic load library and/or other sequence of instructions designed for execution on a computer system. Therefore, some examples describe a non-transitory computer program product having executable program code stored therein for receiving at least one input medical image of a patient in which the patient's lungs are visible. The method further includes processing the at least one input medical image and automatically computing the patient's smoking history based on the at least one input medical image; and outputting the smoking history from the CADx device.

The computer program may be stored internally on a tangible and non-transitory computer readable storage medium or transmitted to the computer system via a computer readable transmission medium. All or some of the computer program may be provided on computer readable media permanently, removably or remotely coupled to an information processing system. The tangible and non-transitory computer readable media may include, for example and without limitation, any number of the following: magnetic storage media including disk and tape storage media; optical storage media such as compact disk media (e.g., CD ROM, CD R, etc.) and digital video disk storage media; non-volatile memory storage media including semiconductor-based memory units such as FLASH memory, EEPROM, EPROM, ROM; ferromagnetic digital memories; MRAM; volatile storage media including registers, buffers or caches, main memory, RAM, etc.

A computer process typically includes an executing (running) program or portion of a program, current program values and state information, and the resources used by the operating system to manage the execution of the process. An operating system (OS) is the software that manages the sharing of the resources of a computer and provides programmers with an interface used to access those resources. An operating system processes system data and user input, and responds by allocating and managing tasks and internal system resources as a service to users and programs of the system.

The computer system may for instance include at least one processing unit, associated memory and a number of input/output (I/O) devices. When executing the computer program, the computer system processes information according to the computer program and produces resultant output information via I/O devices.

In the foregoing specification, the invention has been described with reference to specific examples of embodiments of the invention. It will, however, be evident that various modifications and changes may be made therein without departing from the scope of the invention as set forth in the appended claims and that the claims are not limited to the specific examples described above.

Those skilled in the art will recognize that the boundaries between logic blocks are merely illustrative and that alternative embodiments may merge logic blocks or circuit elements or impose an alternate decomposition of functionality upon various logic blocks or circuit elements. Thus, it is to be understood that the architectures depicted herein are merely exemplary, and that in fact many other architectures can be implemented which achieve the same functionality.

Any arrangement of components to achieve the same functionality is effectively 'associated' such that the desired functionality is achieved. Hence, any two components herein combined to achieve a particular functionality can be seen as 'associated with' each other such that the desired functionality is achieved, irrespective of architectures or intermediary components. Likewise, any two components so associated can also be viewed as being 'operably connected,' or 'operably coupled,' to each other to achieve the desired functionality.

Furthermore, those skilled in the art will recognize that boundaries between the above described operations merely illustrative. The multiple operations may be combined into a single operation, a single operation may be distributed in additional operations and operations may be executed at least partially overlapping in time. Moreover, alternative embodiments may include multiple instances of a particular operation, and the order of operations may be altered in various other embodiments.

However, other modifications, variations and alternatives are also possible. The specifications and drawings are, accordingly, to be regarded in an illustrative rather than in a restrictive sense.

In the claims, any reference signs placed between parentheses shall not be construed as limiting the claim. The word 'comprising' does not exclude the presence of other elements or steps then those listed in a claim. Furthermore, the terms 'a' or 'an,' as used herein, are defined as one or more than one. Also, the use of introductory phrases such as 'at least one' and 'one or more' in the claims should not be construed to imply that the introduction of another claim element by the indefinite articles 'a' or 'an' limits any particular claim containing such introduced claim element to inventions containing only one such element, even when the same claim includes the introductory phrases 'one or more' or 'at least one' and indefinite articles such as 'a' or 'an.' The same holds true for the use of definite articles. Unless stated otherwise, terms such as 'first' and 'second' are used to arbitrarily distinguish between the elements such terms describe. Thus, these terms are not necessarily intended to indicate temporal or other prioritization of such elements. The mere fact that certain measures are recited in mutually different claims does not indicate that a combination of these measures cannot be used to advantage.
malignancy score.

We claim:

1. A method for providing a lung disease risk measure in a Computer Aided Diagnosis (CADx) system comprising:
   receiving an input comprising at least one input image showing all or part of the lungs of a patient;
   analysing the input to identify a feature descriptor comprised of at least one feature group comprised of at least one feature computed from the input image, wherein the at least one feature group describes a characteristic of the image that is not provided as a separate input and correlates to a known clinical predictor of the lung disease;
   calculating a score explanation factor for each feature group, and an overall disease risk score for the patient's risk of lung disease from the feature descriptor; and
   outputting a graphical or textual representation of the overall disease risk score and a corresponding score explanation factor for each feature group, wherein the collection of score explanation factors indicate the proportion to which each characteristic associated with each feature group contributed to the disease risk score; wherein the representation shows which explanation factors have a negative effect on the lung disease risk score, and which explanation factors have a positive effect on the lung disease risk score.

2. A method as claimed in claim 1, wherein the input further comprises one of more of: biomarkers for the patient or clinical parameters for the patient.

3. A method according to claim 2, wherein the biomarkers or clinical parameters comprise: patient age, patient sex, family and clinical history, results of blood tests, and results of lung function tests.

4. A method according to claim 1, wherein the risk score explanation factor is related one or more of tumour size, location and appearance.

5. A method according to claim 1, wherein each at least one feature group comprises a plurality of features for that feature group.

6. A method according to claim 1, wherein the CADx system uses a neural network.

7. A method according to claim 6, wherein the neural network is a convolutional neural network.

8. A method according to claim 1, wherein the overall disease risk score is calculated using a mapping function on the feature descriptor.

9. A computer aided diagnosis lung disease risk measure system comprising:
   an input circuit configured to receive at least one input image showing all or part of the lungs of a patient;
   an analysis and score circuit configured to:
   analyse the at least one input image to identify a feature descriptor comprised of at least one feature group, comprised of at least one feature derived from the input image, wherein the at least one feature group describes a characteristic of the image that is not provided as a separate input and correlates to a known clinical predictor of the lung disease;
   calculate a score explanation factor for each feature group and an overall disease risk score for the patient's risk of lung disease from the feature descriptor;
   an output circuit to output a graphical or textual representation of the overall disease risk score and a corresponding score explanation factor for each feature group, wherein the collection of score explanation factors indicate the proportion to which each characteristic associated with each feature group contributed to the disease risk score; wherein the representation shows which explanation factors have a negative effect on the lung disease risk score, and which explanation factors have a positive effect on the lung disease risk score.

10. A computer aided diagnosis system according to claim 9, wherein the analysis and score circuit further comprises a feature encoder to receive the input image and identify the feature descriptor.

11. A computer aided diagnosis system according to claim 9, wherein the score explanation factor is calculated by applying a mapping function to the feature descriptor.

* * * * *